United States Patent
Guillory et al.

[11] Patent Number: 5,925,889
[45] Date of Patent: Jul. 20, 1999

[54] PRINTER AND METHOD WITH MEDIA GLOSS AND COLOR DETERMINATION

[75] Inventors: Douglas M. Guillory; Michael B. Lloyd; Robert J. Lawton, all of Boise, Id.

[73] Assignee: Hewlett-Packard Company, Palo Alto, Calif.

[21] Appl. No.: 08/956,219

[22] Filed: Oct. 21, 1997

[51] Int. Cl.$^6$ .................................................. G01N 21/86
[52] U.S. Cl. .............................. 250/559.16; 250/223 R; 356/446
[58] Field of Search ................... 250/559.1, 559.16, 250/223 R, 226; 356/445, 446, 448

[56] References Cited

U.S. PATENT DOCUMENTS

| | | | |
|---|---|---|---|
| 3,932,755 | 1/1976 | Sagawa | 250/349 |
| 4,284,356 | 8/1981 | Heilman | 356/429 |
| 4,352,988 | 10/1982 | Ishida | 250/559 |
| 4,555,180 | 11/1985 | Masuda et al. | 356/445 |
| 4,613,235 | 9/1986 | Suga | 356/446 |
| 4,723,072 | 2/1988 | Naruse | 235/454 |
| 4,770,536 | 9/1988 | Golberstein | 356/371 |
| 4,983,854 | 1/1991 | Mizuno et al. | 250/561 |
| 4,989,985 | 2/1991 | Hubble, III et al. | 356/445 |
| 5,004,928 | 4/1991 | Suzuki et al. | 250/559 |
| 5,084,627 | 1/1992 | Ueki et al. | 250/561 |
| 5,117,119 | 5/1992 | Schubert et al. | 250/559 |
| 5,250,813 | 10/1993 | Takahashi et al. | 250/561 |
| 5,401,977 | 3/1995 | Schwartz | 250/559.1 |
| 5,414,269 | 5/1995 | Takahashi | 250/561 |
| 5,459,580 | 10/1995 | Suzuki | 358/296 |
| 5,552,890 | 9/1996 | Nanna et al. | 356/448 |

OTHER PUBLICATIONS

TAPPI Standard T480 om–92, "Specular Gloss of Paper and Paperboard at 75 Degrees", 1992, pp. 1–7.

*Primary Examiner*—Stephone Allen

[57] ABSTRACT

A printer responds to a media gloss measurement for improved color printing. The printer includes a gloss meter, a controller, and a print engine. The gloss meter includes a solid body having a source tube and a reflection tube each being integral within the body. An LED in the source tube illuminates a reference surface at an angle of incidence. A photo sensor in the reflection tube responds to a first reference spectral reflection from the surface at an angle of reflection equal to the angle of incidence. When a sheet of media is registered by the printer against the reference surface, the photo sensor responds to a second spectral reflection from the media. The ratio of second to first spectral reflection intensities is compared to a selected threshold to identify the media by gloss level. When motion of the media is resumed, the media wipes the reference surface to maintain the accuracy of gloss measurements. The angle of incidence is less than thirty degrees for discriminating among media having low gloss characteristics.

20 Claims, 6 Drawing Sheets

PRINTER AND METHOD WITH MEDIA GLOSS AND COLOR DETERMINATION

FIELD OF THE INVENTION

Embodiments of the present invention relate to printers and to systems for printing an image on media where a measure of the media surface governs printing for higher quality results.

BACKGROUND OF THE INVENTION

As an introduction to problems solved by the present invention, consider the conventional electrophotographic printer employed in office computing systems, facsimile receivers, office copiers and the like. Such a printer typically includes one or more input trays for paper on which to print. Although some printers are designed to operate exclusively with one type of print media, contemporary users are demanding the versatility to print on a wide variety of sheet media including papers that are colored, coated, or otherwise treated, overhead transparencies, plastic sheet, and other resin films, to name a few examples. Methods of achieving high resolution, permanent, high-speed print on these media vary, however.

Conventional printers equipped with media sensors discriminate among media only when media are widely different, such as discriminating a transparency from opaque paper. In such printers, a signal from the sensor affects a selection of a print mode among several built-in print modes. Neither the method of sensing nor the method of selection is accurate or repeatable enough to adjust high quality printing on papers having slight variations in surface gloss.

Inaccuracy and non-repeatability are attributable to many factors. When light sources and sensors are used to make surface measurements, thermal and aging factors degrade measurement accuracy. Thermal factors degrade alignment, adversely affecting accuracy. Because temperature within a printer varies greatly during operation, thermal factors, degrade repeatability. Furthermore, within the conventional printer, debris including toner, paper fragments, and dirt may temporarily or permanently build on portions of the measurement system, making measurements inaccurate and non-repeatable.

The market for high resolution, permanent, high-speed printers is already large and growing with the increase in computing power available at decreasing cost. In addition, the variety of media available to the user is increasing as the user increases in sophistication. Heretofore, only book and periodical publishers and professional printers were concerned with presenting printed results on a media of selected gloss appearance. Now, however, users are expecting to be able to produce equivalent results on sequential sheets of any media used professionally, with little or no intervention with the printing method.

In view of the problems described above and related problems that consequently become apparent to those skilled in the applicable arts, the need remains in printers and in systems for printing an image on media for accurate measurement of the media surface in order to govern printing for higher quality results.

SUMMARY OF THE INVENTION

Accordingly, a printer in one embodiment of the present invention includes a reference surface, a gloss detector, a controller, and a print engine. The printer prints on a provided sheet. The gloss detector measures a first reflection from the reference surface and a second reflection from the sheet. The controller provides a signal to adjust the print engine in response to gloss detector measurements.

Improved printing on a wide variety of media results from improved accuracy and repeatability of the gloss detector. Variations in media gloss, color, and texture that degrade print quality have been detected and compensated by use of the present invention. According to a first aspect of such an embodiment, the reference surface remains clean of toner, paper fragments, and the like. According to another aspect, a ratio of measurements compensates for operating temperature drift and aging drift in the gloss detector components.

The controller and print engine cooperate in response to reflection measurements in various embodiments of the present invention for high quality printing on media having slight variations in surface gloss. In electrophotographic printer embodiments and ink jet printer embodiments, a ratio of reflection measurements is used by the controller to adjust one or more of several parametric printer settings.

In still another embodiment, the controller directs media to be rejected, on a sheet by sheet basis, as unsuitable for printing as a consequence of inappropriate values of the ratio of reflection measurements.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims.

In each functional block diagram, a broad arrow symbolically represents a group of signals that together signify a binary code. For example, a group of address lines is represented by a broad arrow because a binary address is signified by the signals taken together at an instant in time. A group of signals having no binary coded relationship is shown as a single line with an arrow. A single line between functional blocks represents one or more signals.

A person having ordinary skill in the art will recognize where portions of the figures have been expanded to clarify the presentation.

DETAILED DESCRIPTION OF THE PREFERRED EMBODIMENT

Figure 1:
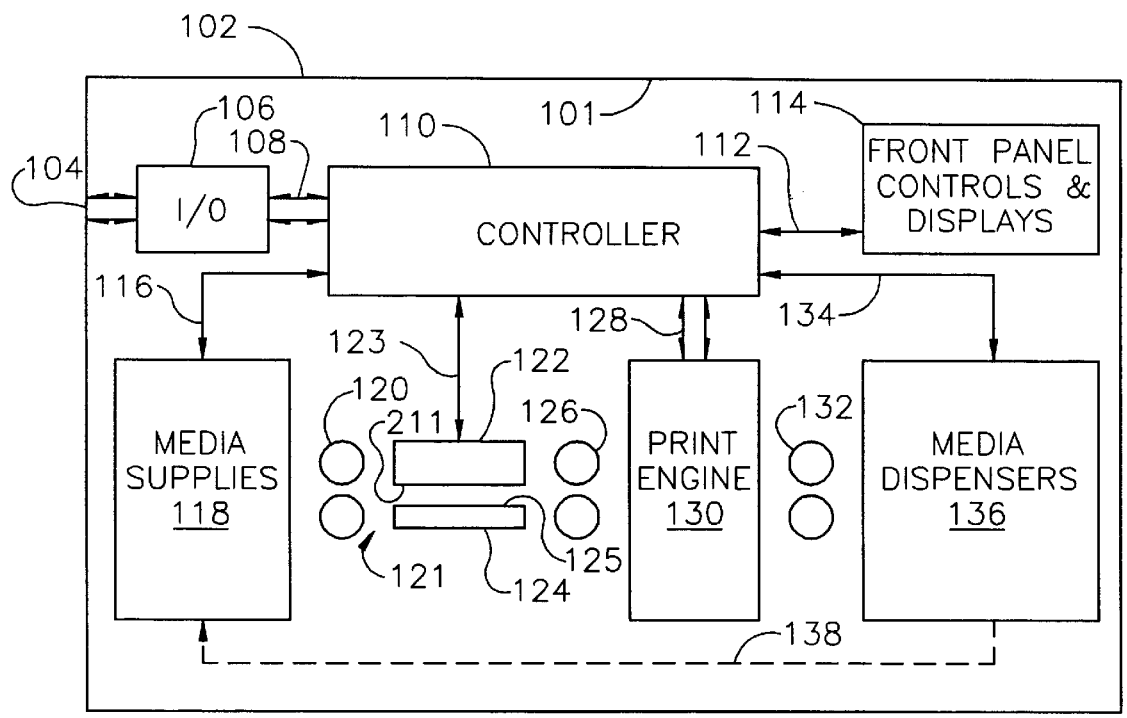
FIG. 1 is a functional block diagram of a printer in one embodiment of the present invention.

FIG. 1 is a functional block diagram of a printer in one embodiment of the present invention. Printer 102 primarily includes input/output logic 106, controller 110, front panel controls and displays 114, media supplies 118, a print engine 130, and media dispensers 136 within enclosure 101. Printer 102 also includes gloss meter 121 arranged between media transports 120 and 126.

Bus 104 couples printer 102 to a conventional computer system, not shown. Bus 104 conveys image description signals to the printer and status signals from the printer. Data describing an image to be printed is received on bus 104 by input/output logic 106. Bus 104 and input/output logic 106 are of conventional structure and operation. Data describing an image to be printed conform to a conventional protocol such as the PCL printer language marketed by the Hewlett-Packard Company.

Controller 110 responds to PCL instructions to direct substantially all printer functions and to report status via front panel controls and displays 114 and PCL responses. Controller 110 cooperates with input/output logic 106 via bus 108. Bus 108 is of conventional structure and operation.

When enabled by front panel controls 114 received on line 112, controller 110 formats an image to be printed. Formatting operations include conventional formatting such as processing scalable fonts, color and edge enhancement, and overlapping images.

When prepared to begin printing the formatted image, controller 110 reads the status of media supplies 118 and directs provision of a sheet of media from a particular supply on line 116, as directed in the conventional manner by PCL commands, front panel controls, or supply availability. A sheet of media then enters the so-called "paper path," though the same path is traversed by a sheet of media of any type. The paper path includes transports 120 and 126 that direct the sheet into print engine 130 and includes transport 132 and return path 138. Return path 138 schematically represents the portion of a conventional paper path needed for two-sided printing through a one-sided print engine.

As to controller 110, the media entering transport 120 is of uncertain type and of unknown surface characteristics. Although the origin tray or bin of media supplies 118 that was directed to supply the media may be presumed to contain only media of one known type, controller 110 determines the media type and surface characteristics of each particular sheet prior to printing. This determination is made in cooperation with gloss meter 121, coupled to controller 110 by line 123. A measurement using gloss meter 121 is an accurate and reliable basis for adjusting print engine parametric settings. According to the present invention, appropriate print engine adjustments are made based on the signal returned on line 123 from gloss meter 121.

Gloss meter 121 includes gloss detector 122 and reference surface 124. Gloss detector 122 includes a light source, and a light detector. Light sourced by gloss detector 122 illuminates a portion of reference surface 124 at an angle of incidence. Gloss detector 122 receives light at an equal angle of reflection and provides a signal on line 123 proportional to the intensity of the light received. Provision of the signal on line 123, as analyzed by controller 110, accomplishes a first measurement.

After the first measurement is completed, transport 120 moves the sheet, not shown, so that the sheet is interposed between reference surface 124 and gloss detector 122. Cooperation of transports 120 and 126 ensure that the sheet is flat during a second measurement. Ensuring that the sheet is flat is accomplished in one of four different ways. In a first embodiment, transport 120 halts motion of the sheet while a second measurement is made. In a second embodiment, transport 120 moves the sheet until the sheet enters transport 126; whereupon transports 120 and 126 cooperate to provide a lateral tension in the sheet. In a third embodiment, the second measurement is made while the sheet is being moved at the maximum rate for transport. In a fourth embodiment, the second measurement is made while the sheet is being moved at a rate less than the maximum rate for transport. Selection of an appropriate embodiment for a particular application is based on structural properties of the media likely to be encountered, mechanical tolerances and orientation of the paper path, the need to perform conventional registration concurrent with transport, and fixed or parametric printing speeds appropriate for print engine 130.

When the sheet is interposed between gloss detector 122 and reference surface 124 and held flat, light sourced by gloss detector 122 illuminates a portion of the sheet at an angle of incidence. Gloss detector 122 receives light at an equal angle of reflection and provides a signal on line 123 proportional to the intensity of the light received. Provision of the signal on line 123, as analyzed by controller 110, accomplishes a second measurement.

After the second measurement is made, the sheet is moved by transport 126 from between reference surface 124 and gloss detector 122 and into print engine 130. While in motion against reference surface 124, the sheet, in contact with the surface, moves debris off of the surface, thereby cleaning the surface.

Reference surface 124 includes conductive material so as to dissipate static electricity which may otherwise build up due to friction of the media and the surface, or movement of cooling air within enclosure 110. In one embodiment, reference surface 124 is a polished stainless steel. In alternate embodiments, reference surface 124 includes other metals, conventional mirror deposits, or when principally made of a plastic, sufficient carbon or other conductive particles or fibers to dissipate static charges. A latent static charge on reference surface 124 in one embodiment helps to maintain the sheet in a flat or otherwise prescribed orientation for accurately making the second measurement.

Controller 110 calculates a ratio of the first and second measurements, determines the media type, and then either directs the media to be printed by print engine 130 in a way prescribed by controller 110, or directs the media to be rejected. This procedure in one embodiment is discussed in detail below with reference to FIG. 5. Controller 110 includes conventional digital and analog electronic circuits arranged to perform the special functions of the present invention.

Print engine 130 is of a conventional electrophotographic type. Print engine 130 includes additional drive apparatus, not shown, for moving the sheet on the portion of the paper path that goes through print engine 130. The rate of movement of the sheet along this portion of the paper path is directed by controller 110.

After printing, transport 132 moves the printed sheet into media dispensers 136 where the sheet becomes available to the user as a result of printing. Media dispensers 136 provide status and respond to controls in cooperation with controller 110 via line 134. Controller 110 directs the sheet to a particular dispenser or to return path 138 in response to PCL commands, front panel controls, or availability. Media dispensers 136 are of conventional design and function in cooperation with controller 110 in a conventional manner. Media dispensers 136 are arranged for efficient user access and not necessarily within enclosure 101, as shown schematically in FIG. 1.

Figure 2:
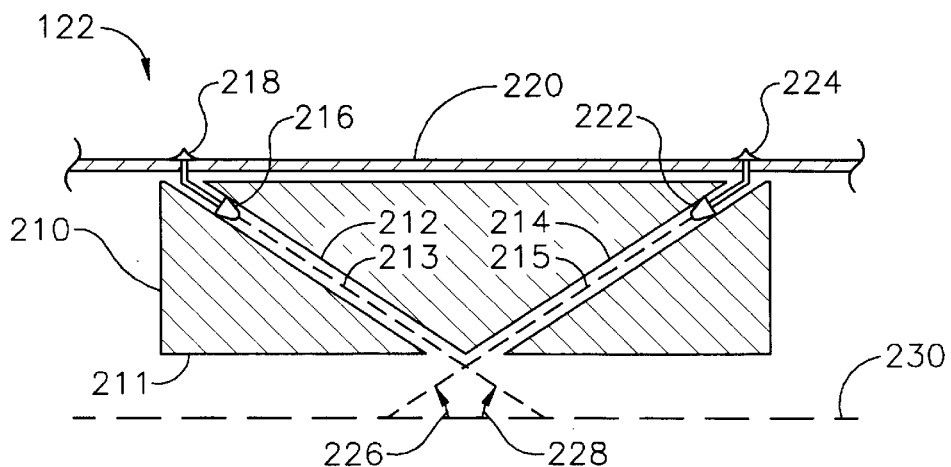
FIG. 2 is a cross section of the gloss detector of the printer of FIG. 1.

FIG. 2 is a cross section of gloss detector 122 shown in FIG. 1. Gloss detector 122 primarily includes block 210 conventionally attached to printed circuit board 220. Source tube 212 on axis 213 and reflection tube 214 on axis 215 are formed in block 210 by conventional techniques including casting and boring. Light source 216 is soldered to printed circuit board 220 at fillet 218 and is located in tube 212. Source 216 is of the conventional type including, for example, a light emitting diode or laser diode providing visible, infrared, or ultraviolet light. Light sensor 222 is soldered to printed circuit board 220 at fillet 224 and is located in tube 214. Sensor 222 is of the conventional type including, for example, a photocell, a photoresistor, or a photomulitplier.

The diameter of tubes 212 and 214 need not be identical, but are preferably small in relation to axial length. In one embodiment, tube diameters are equal and in the range 0.025 to 0.4 inches, preferably about 0.1 inches.

Several mechanical variations are feasible for detector 122. In a first embodiment tubes 212 and 214 are open to ambient air. Walls of the tubes absorb light so that only the spectral reflection is detected at sensor 222. Tube 214 operates as one example of a means for rejecting diffuse reflected light. In a second embodiment, tube 212 includes a reflective surface for guiding a larger percentage of incoherent light out of tube 212. In a third embodiment, tubes 212 and 214 are filled with transparent material to prevent partial or complete obstruction by debris. In a fourth embodiment, tubes 212 and 214 are directed downward so that debris will fall with gravity out of tubes 212 and 214. In a fifth embodiment, block 210 includes a conductive material or is formed entirely of a metal to dissipate static electricity. In alternates to the above embodiments, tubes 212 and 214 are formed of metal having reflective rather than absorptive surfaces.

Axis 213 intersects specimen plane 230 at angle 228, referred to herein as the angle of incidence. Axis 215 intersects specimen plane 230 at angle 226, referred to herein as the angle of reflection. Tubes 212 and 214 are formed so that the angles 228 and 226 are substantially equal. By orienting axis 215 at angle 226, diffuse reflected light is rejected and sensor 222 responds primarily to spectral reflected light. In an embodiment preferred for accurately identifying media having low gloss (matte) characteristics, angle 228 is between 5 and 30 degrees, preferably about 20 degrees.

Specimen plane 230 is parallel to reference surface 124 (shown in FIG. 1) and the top surface of the sheet when interposed between reference surface 124 and detector 122. The distance (vertical in FIGS. 1 and 2) between top 125 of reference surface 124 and bottom surface 211 of detector 122 is made large compared to the expected maximum thickness of media to minimize measurement error among media of various thicknesses. In one embodiment this distance is in the range 0.1 to 0.75 inches, preferably 0.5 inches.

Figure 3:
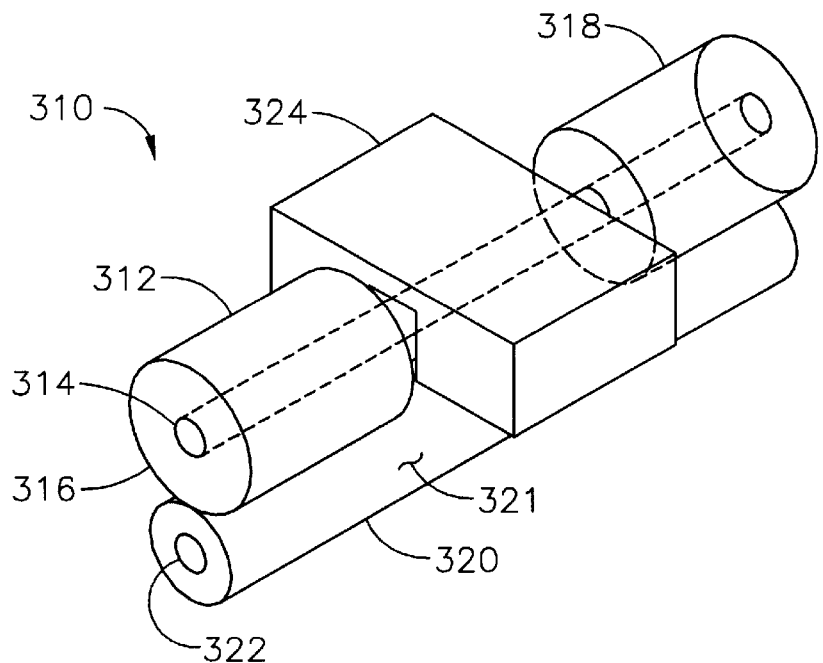
FIG. 3 is a perspective view of an alternate gloss meter for use in the printer of FIG. 1.

FIG. 3 is a perspective view of an alternate gloss meter used in place of gloss meter 121 in the printer of FIG. 1. Gloss meter 310 includes registration roller 320, tension roller 312, and gloss detector 324. Registration roller 320 is controlled by controller 110 in a conventional manner for aligning the front edge of the media for proper positioning of the printed image by print engine 130. In the embodiment shown, registration roller 320 is of stainless steel and provides reference surface 321 directly under detector 324.

Rollers 320 and 312 rotate on axles 322 and 314 respectively in parallel pinching relationship. As a sheet is moved between rollers 320 and 312, debris adheres to the back side of the sheet or is rubbed by the sheet and so is moved off reference surface 321 so as to clean reference surface 321. Additional rollers, such as roller 318, are arranged by a conventional technique along axle 314 as needed to provide tension in the sheet, move the sheet, and register the sheet.

Figure 4:
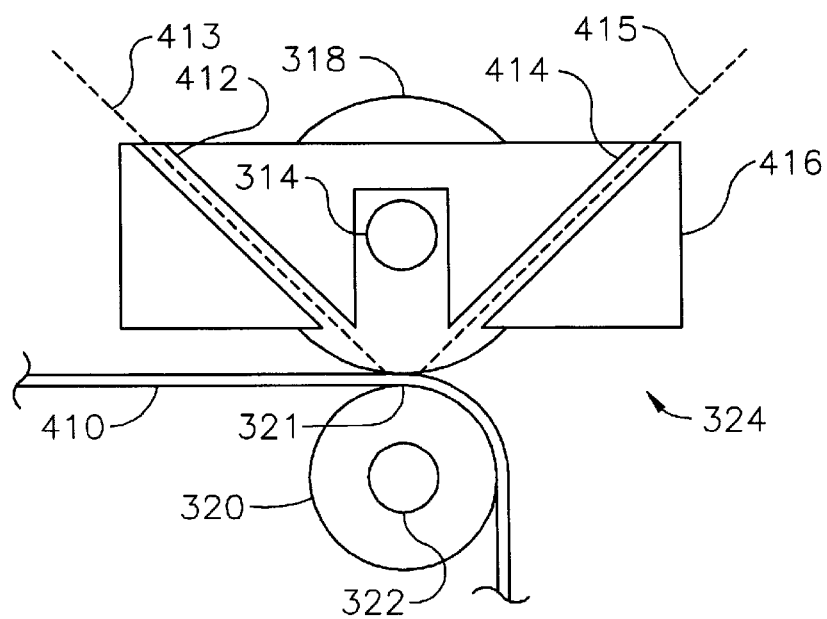
FIG. 4 is a cross section of the gloss detector of FIG. 3.

FIG. 4 is a cross section of gloss detector 324 of FIG. 3 with media 410 shown interposed between detector 324 and registration roller 320. Gloss detector 324 includes block 416 having cast tubes 412 and 414 with respective axis 413 and 415. Block 416 is shaped to straddle axle 314 so that equal angles of incidence and reflection are less than 30 degrees each. Measurements made with detector 324 have substantially no error attributable to the thickness of the media because reference surface 321 when media is absent and the top surface of media 410 when present are at substantially the same position with respect to axis 413 and 415.

Figure 5:
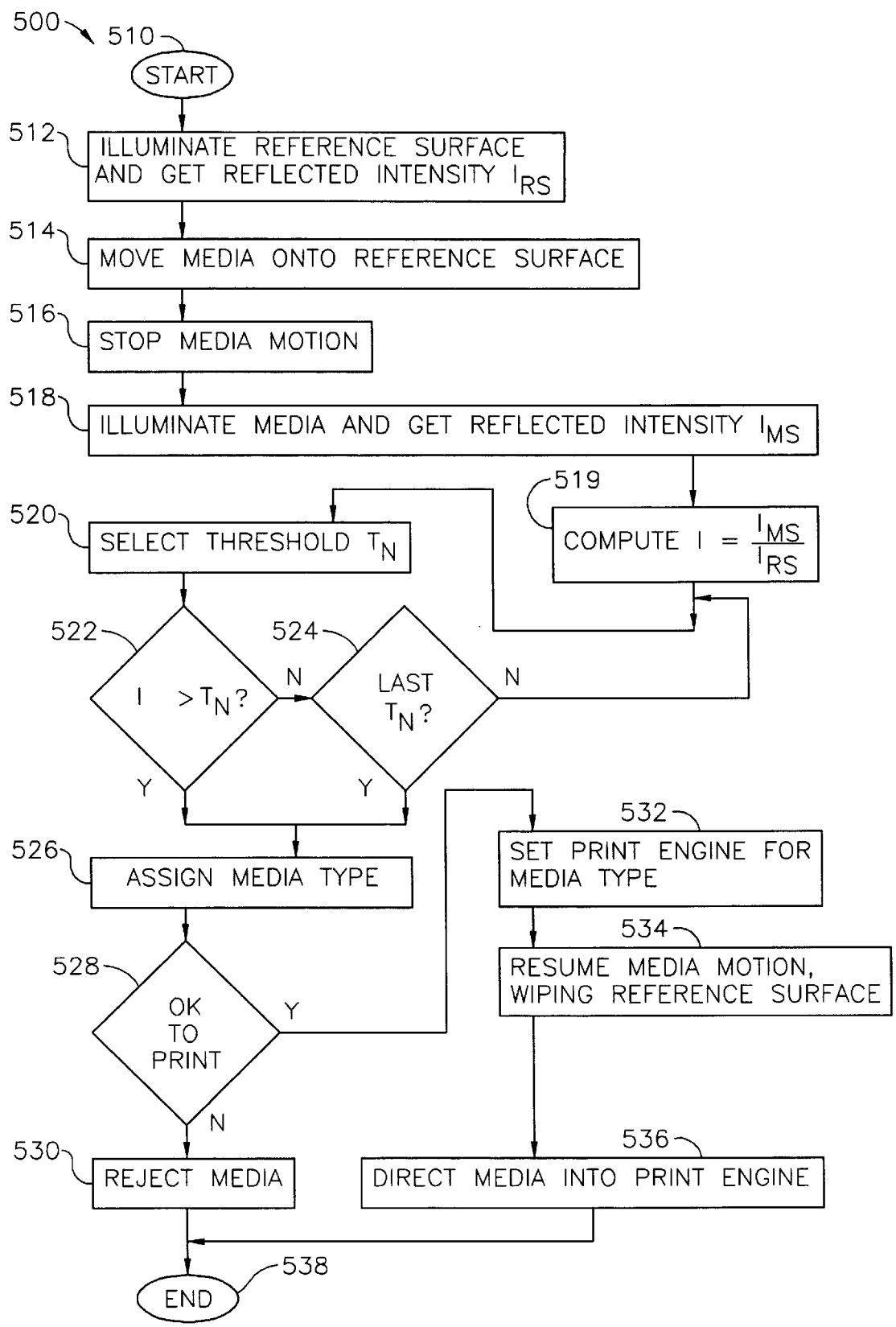
FIG. 5 is a flow chart of a method of printing in one embodiment of the present invention.

FIG. 5 is a flow chart of a method of printing in one embodiment of the present invention. References to FIGS. 1 through 4 are made to structures in various printer embodiments which cooperate to perform the method of FIG. 5. Method 500 is performed in one embodiment by controller 110 of printer 102.

For each sheet of media to be printed, method 500 begins at step 510. At step 512, the reference surface is illuminated and the spectral reflection intensity at sensor 222 is measured and assigned to variable $I_{RS}$. This constitutes a first measurement. Illumination in one embodiment is continuous to stabilize light source intensity. Illumination in alternate embodiments is multiplexed, pulsed, or turned on when needed so as to conserve power and limit temperature rise so as to avoid measurement errors due to expansion of materials.

At step 514 the sheet is moved onto the reference surface. At step 516, sheet movement is stopped. In alternate embodiments sheet movement may continue at the same or a different rate.

At step 518, the sheet is illuminated and the spectral reflection intensity at sensor 222 is measured and assigned to variable $I_{MS}$. This constitutes a second measurement. Illumination in one embodiment is continuous from the time of the first measurement. Illumination in alternate embodiments is multiplexed, pulsed, or turned on when needed so as to conserve power as discussed above.

At step 519, a normalized intensity I is computed as the ratio of $I_{MS}$ divided by $I_{MR}$. The ratio normalizes the second measurement to compensate for degradation of the light source and light sensor of the gloss detector.

At step 520, a threshold is selected from a plurality of thresholds, the selected threshold being identified as $T_N$. In a first embodiment, only one threshold is used because only matte paper and glossy overhead transparencies are expected as media. In alternate embodiments including color printers, a set of predetermined thresholds is available to controller 110. In one such embodiment, controller 110 includes these thresholds in internal memory. In an alternate embodiment, user-selected thresholds are provided via bus 104, input/output logic 106, and bus 108 in response to PCL commands. In yet another embodiment, thresholds are identified, by selection or specification, via front panel controls and displays 114 via line 112.

At step 522, controller 110 compares the normalized intensity I to the selected threshold $T_N$. Since thresholds are selected in descending order, when the normalized intensity of the reflection from the media is greater than the threshold, the media type is identified and a variable conveying that information, MT, is assigned an appropriate value at step 526. When the result of the comparison at step 522 is false, then at step 524, the remaining thresholds are selected one at a time. If none is found to apply, a default value for MT is assigned at step 526.

At step 528, the identified media type is compared to the current capability of the printer. If the printer is currently configured to print on the identified media, or if reconfiguration is desirable and feasible, printing will be attempted by proceeding to step 532.

At step 530, media is rejected as unprintable. In alternate embodiments additional functions accompany rejection such as raising an audible or visible alarm at front panel controls 114, communicating with the computer connected to bus 104 via PCL commands, or simply counting the number of rejections over time until a limit is exceeded whereupon one or more of such actions is taken. Control from step 530 passes to step 538, the end of method 500 for one sheet of media.

At step 532, the sheet has been determined to be printable and consequently, one or more parametric settings of the print engine are adjusted. An electrophotographic print engine embodiment includes a conventional developer, drum, transfer belt or roller, fuser, toner dispenser, excess toner removal system, and media driver apparatus through the print engine. For such a print engine, a parametric setting includes, for example, a developer bias voltage or current; a drum rotation speed, or charge/discharge voltage or current; a transfer belt or roller speed, or charge/discharge voltage or current, a fuser temperature, a toner dispensing rate; a toner removal rate; a rate that media is driven through the print engine, or a combination of such parametric settings. One set of adjustments is made in an electrophotographic color printer for each color to be printed. An ink jet print engine embodiment includes an ink dryer and media driver apparatus through the print engine. For such a print engine, a parametric setting includes, for example, an amount of ink to be dispersed, a dryer temperature, a rate that media is driven through the print engine, or a combination of such parametric settings. For a color ink jet printer, one set of adjustments is made for each color to be printed. Step 532 includes a delay in one embodiment to assure that the print engine is prepared to print as adjusted.

An adjustment is made in one of several alternate ways. In a first embodiment the adjustment is made by setting a parameter of the print engine to a predetermined value identified by the media type MT. In a second embodiment the adjustment at step 532 is made by setting a parameter of the print engine to a calculated value based on the normalized intensity $I_N$ rather than with reference to media type MT. In a variation of this second embodiment, steps 520 through 530 are omitted, and control passes from step 519 to step 532. In a third embodiment, adjustment of a parametric setting is proportional to normalized intensity $I_N$. In a fourth embodiment adjustment follows a conventional table look up algorithm with interpolation.

In the illustrated embodiment, at step 534, motion of the sheet is resumed. Note that because the media has been in contact with the reference surface and that at step 534 the sheet is moving away from the reference surface, the sheet provides a wiping action that cleans the reference surface. In an embodiment wherein the print engine includes a conventional electrophotographic print engine, the wiping action of the sheet is sufficient to clean toner from the reference surface. In other embodiments, other debris is consequently removed. Debris, including toner, need not adhere to the back side of the sheet. In an alternate embodiment, debris and toner are removed from the region of the reference surface and the sheet by techniques including friction, air turbulence, filtering, or an electrostatic field.

At step 536, the sheet is directed into the print engine to be printed. The print engine's internal drivers move the sheet on the paper path at the rate prescribed for proper printed results.

At step 538, method 500 is completed for the sheet that has been printed. Method 500 is repeated as needed to print on additional sheets of media.

Figure 6:
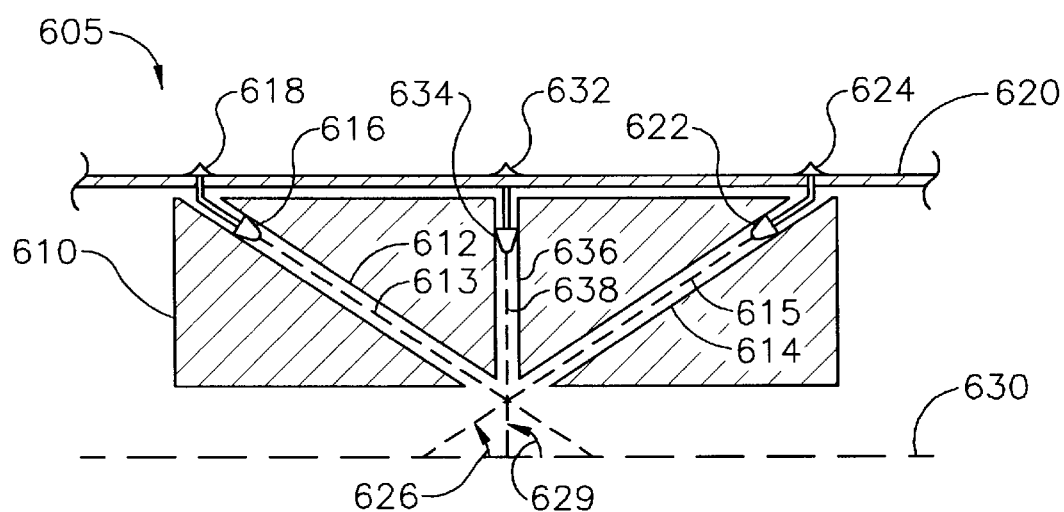
FIG. 6 is a cross section of an alternate gloss detector used in place of gloss detector 210 of FIG. 2.

FIG. 6 is a cross section of an alternate gloss detector 605 used in place of gloss detector 210 in FIG. 2. Numbered elements in FIG. 6 correspond in structure and function to elements in FIG. 2 numbered less four hundred, except as shown and discussed below.

Gloss detector 605 includes reflection tube 636 on axis 638 formed in a manner similar to source tube 612 or reflection tube 614. Light sensor 634 is soldered to circuit board 620 at fillet 632 and is of a type similar or identical to light sensor 622. By locating reflection tube 636 to receive light on an axis 638 at an angle 629, shown approximately perpendicular to specimen plane 630, light received is diffuse rather than spectral. Tube 636 operates as one example of a means for rejecting spectral reflected light.

In alternate embodiments, reflection tube 636 is located on an axis at any value of angle 629 from about 0 to about 180 degrees within the limits of manufacturing of reflection tube 636 in block 610. In a preferred embodiment, angle 629 differs from angle 626 by about 15 degrees. In another alternate embodiment, reflection tube 614 and sensor 622 are omitted. Selection of one or two reflection tubes and selection of the angle 626 for diffuse reflection sensing depend on the expected variety of media, color variation, texture variation, and the accuracy and repeatability of print engine adjustment needed to achieve the desired level of print quality.

Figure 7:
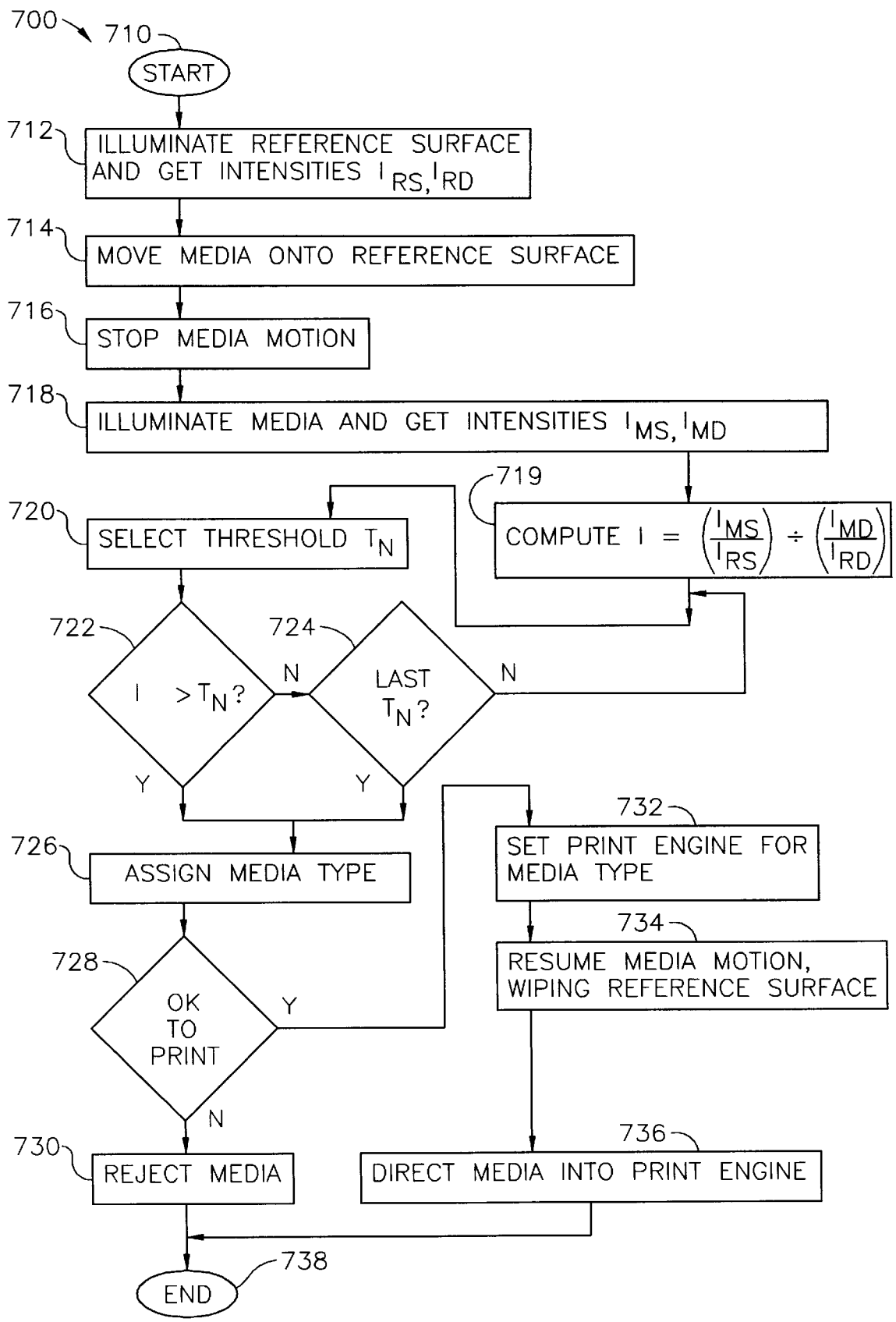
FIG. 7 is a flow chart of an alternate method used in place of the method of FIG. 5.

FIG. 7 is a flow chart of an alternate method 700 used in place of method 500 shown and described with reference to FIG. 5. Method 700 takes advantage of the diffuse light sensing arrangement of gloss detector 605 shown and described with reference to FIG. 6. Numbered steps in FIG. 7 correspond in function to steps in FIG. 5, numbered less two hundred, except as shown and discussed below.

At step 712, the spectral and diffuse light intensities reflected by the reference surface into sensors 622 and 634 are measured and assigned to variables $I_{RS}$ and $I_{RD}$ respectively for a first measurement.

At step 718, the spectral and diffuse light intensities reflected by the media into sensors 622 and 634 are measured and assigned to variables $I_{MS}$ and $I_{MD}$ respectively for a second measurement.

At step 719, the normalized intensity I is computed by dividing normalized spectral reflection by normalized diffuse reflection. In alternate embodiments, intensity measurements are combined by linear and nonlinear techniques including, for example, a power series or techniques optimized for computing speed or simplicity.

Method 700 provides improved media discrimination over method 500 shown in FIG. 5. The techniques used in alternate embodiments for method 500 apply similarly to define alternate embodiments for method 700.

Operation of the above embodiments has been directed to adjustment of printing in response to variation in paper gloss. In alternate embodiments, printing is adjusted in response to variation in media color. To detect media color, light intensity measurements by a gloss meter are made first at one light wavelength and again at a second wavelength.

For example, a color detecting gloss meter substituted for gloss meter 122 shown in FIG. 2 includes an alternate light source for light source 216 that provides light in more than one wavelength. Such a light source in one embodiment consists of a conventional pair of light emitting diodes individually illuminated. As a second example, a color detecting gloss meter substituted for gloss meter 605 shown in FIG. 6 includes a similar alternate light source for light source 616.

As a further example of a color detecting gloss meter, gloss meter 605 is modified to include a broad band light source for light source 616 and two different narrow band light sensors for sensors 622 and 634. In an alternate embodiment, sensors 622 and 634 are broad band, but tubes 614 and 636 include filters that absorb light not to be included in the intensity measurement by the respective sensor.

Figure 8:
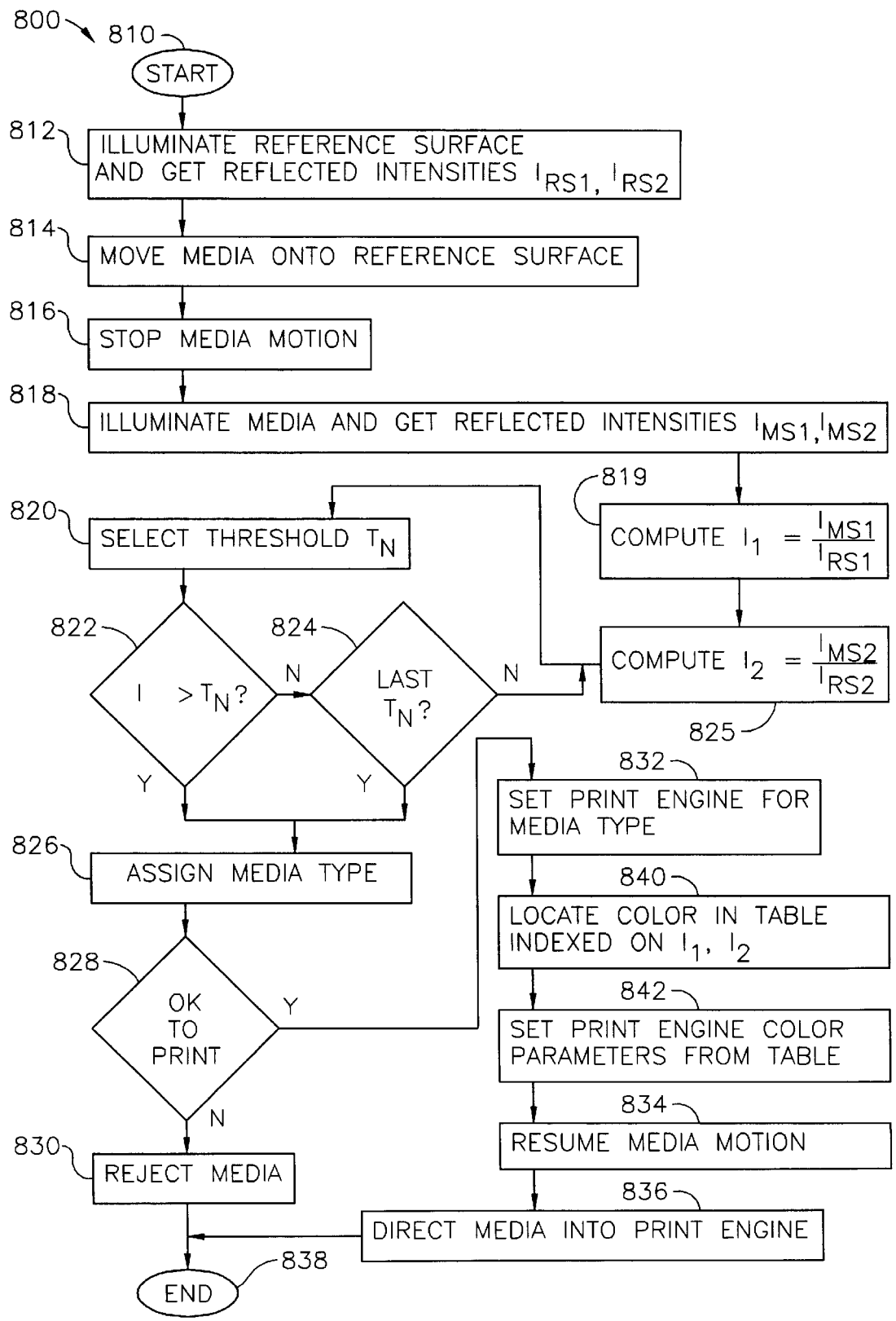
FIG. 8 is a flow chart of a method for color printing in one embodiment of the present invention.

FIG. 8 is a flow chart of a method 800 for color printing used in place of method 500 shown and described with reference to FIG. 5. Method 800 takes advantage of the color detecting gloss meters described above. Numbered steps in FIG. 8 correspond in function to steps in FIG. 5, numbered less three hundred, except as shown and discussed below.

At steps 812 and 818, spectral reflected intensities at two wavelengths are measured respectively from the reference surface and the media. Illumination may be simultaneous at both wavelengths or provided first at one wavelength and then at the second wavelength.

At steps 819 and 825, two normalized intensities are computed using the values measured in steps 812 and 818 at each of two wavelengths. The value to be used as intensity I in step 822 in a first embodiment is $I_1$; in a second embodiment, $I_2$; and in a third embodiment, an average of $I_1$ and $I_2$. The appropriate value to use as intensity I depends on the relationship between gloss and illumination wavelength for the expected range of media.

At step 840, after media gloss is accounted for, intensities $I_1$ and $I_2$ are used as indexes into a table of media colors stored in controller 110.

At step 842, data from the table is read and used to set parametric printer settings for proper color reproduction on media of the identified color. These data describe the amount of primary color toner needed for printing. Data in the table is obtained from empirical toner and media studies.

The foregoing description discusses preferred embodiments of the present invention, which may be changed or modified without departing from the scope of the present invention.

For example, the printer of FIG. 1 in alternate embodiments with conventional design modifications constitutes a copier, a facsimile machine, or a combination printer, copier, and facsimile machine.

Gloss meter 121 in alternate embodiments does not precede print engine 130 but is integral thereto, located for example, prior to a gloss-sensitive process step performed by print engine 130.

Although tubes 212, 214, 412, and 414 are shown integral to a detector body, in alternate embodiments, separate tubes are formed and mechanically aligned with respect to the reference surface by conventional techniques for lower cost manufacture, sparing, and maintenance.

Controller 110 in alternate embodiments is formed by reprogrammable digital logic, programmed in response to data received via input/output logic 106. In still further embodiments, gloss meters described above include integral computation circuitry to perform a portion or all of methods 500, 700 or 800.

Alternative means for rejecting diffuse or spectral light include conventional techniques such as lenses, prisms, aligned slits, tubes, polarizers, combinations thereof and equivalents.

Methods 500, 700 and 800 describe actions taken on the basis of individual measurements for each quantity, for example $I_{RS}$, $I_1$, I, etc. Alternate embodiments having greater accuracy employ similar methods modified to obtain multiple measurements for each such quantity and compute an average or filtered quantity to be used, for example, in further computation, comparison, data selection, and parametric settings.

These and other changes and modifications are intended to be included within the scope of the present invention.

While for the sake of clarity and ease of description, several specific embodiments of the invention have been described; the scope of the invention is intended to be measured by the claims set forth below. The description is not intended to be exhaustive or to limit the invention to the form disclosed. Other embodiments of the invention will be apparent to one of ordinary skill in the art to which the invention applies by reference to the description of the invention and referenced drawings or by practice of the invention.

The words and phrases used in the claims are intended to be broadly construed. The word "tube" includes a conduit having any geometric cross section including circular, oval, and rectangular, for example. A "signal" refers to mechanical and/or electromagnetic energy conveying information. When elements are "coupled," a signal can be conveyed in any manner feasible in light of the nature of the coupling. For example, if several electrical conductors couple two elements, then the relevant signal comprises the energy on one, some, or all conductors at a given time or time period. When a physical property of a signal has a quantitative measure and the property is used by design to control or communicate information, then the signal is said to be characterized by having a "value." The relevant property may be instantaneous or an average. A "parameter" or "parametric setting" takes a quantity value selected from a range of values. An analog parameter would take a real number value and a digitized parameter would take a fixed precision value from a predetermined range of such fixed precision values.

What is claimed is:

1. A printer that prints on a plurality of sheets, the printer comprising:
   a. a gloss meter that, prior to printing each sheet of the plurality, provides a first measurement at a respective first time and a second measurement at a respective second time, the meter comprising:
      (1) a light source;
      (2) a reference surface; and
      (3) a light detector, the first measurement being responsive to light detected during the first time reflected from the reference surface;
   b. a handler that individually routes each sheet, each sheet interposed between the meter and the reference surface during the second time, the second measurement being responsive to light detected during the second time reflected from each respective sheet;

c. a print engine that receives each sheet from the handler; and d. a control system that receives printing control data, directs operation of the print engine in response to the data, and adjusts a parametric setting of the print engine in response to the first measurement, and the second measurement.

2. A printer that prints on a provided sheet, the printer comprising:

a. a reference surface;

b. a gloss detector responsive to a first specular reflection from the surface and to a second specular reflection from the sheet;

c. a controller, coupled to the detector, that provides a signal responsive to a ratio of the first reflection and the second reflection;

d. a print engine that prints on each sheet; and e. a sheet handler that routes each sheet through the print engine at a velocity responsive to the signal.

3. A printer that prints on a provided sheet, the printer comprising:

a. a reference surface;

b. a gloss detector responsive to a first reflection from the surface and to a second reflection from the sheet;

c. a print engine that prints on the sheet in response to a signal; and d. a controller, coupled to the detector and to the print engine, that provides the signal for adjusting a parametric setting of the print engine in response to a ratio of the first reflection and the second reflection.

4. The printer of claim 3 wherein the gloss detector comprises a body having an integral source tube and an integral reflection tube.

5. The printer of claim 3 further comprising a sheet handler responsive to the controller for moving each sheet individually across the reference surface.

6. The printer of claim 3 further comprising a sheet handler responsive to the controller for moving each sheet individually across the reference surface.

7. The printer of claim 3 further comprising a sheet handler responsive to the controller for moving each sheet individually across the reference surface.

8. The printer of claim 5 wherein the handler is coupled to the controller, the controller provides a second signal in response to the ratio, and the second velocity is responsive to the second signal.

9. The printer of claim 7 wherein the handler stops sheet motion while the gloss detector receives the second reflection.

10. The printer of claim 5 wherein the handler comprises a registration roller comprising the reference surface.

11. The printer of claim 3 wherein the gloss detector comprises means for rejecting diffuse reflected light.

12. The printer of claim 3 wherein the gloss detector comprises means for rejecting spectral reflected light.

13. The printer of claim 3 wherein the signal is responsive to a comparison of the ratio to a threshold.

14. The printer of claim 12 wherein the controller further comprises an input channel that provides a second signal that identifies the threshold.

15. The printer of claim 3 wherein the parametric setting comprises a temperature.

16. The printer of claim 3 wherein the parametric setting comprises a voltage.

17. The printer of claim 3 wherein:

a. the gloss detector illuminates the surface and the sheet at an angle of incidence and receives the first reflection and the second reflection at an angle of reflection; and b. the angle of incidence is substantially equal to the angle of reflection.

18. The printer of claim 17 wherein:

a. the illumination from the gloss detector comprises a first wavelength at a first time and a second wavelength at a second time; and b. the controller provides the signal in response to:

(1) a first ratio of the first reflection and the second reflection at the first time; and (2) a second ratio of the first reflection and the second reflection at the second time.

19. The printer of claim 3 wherein:

a. the gloss detector illuminates the surface and the sheet at an angle of incidence, receives the first reflection at a first angle of reflection, and receives the second reflection at the first angle of reflection;

b. the angle of incidence is substantially equal to the angle of reflection;

c. the gloss detector further receives a third reflection from the sheet at a second angle of reflection different from the first angle of reflection; and d. the controller is further responsive to the third reflection for providing the signal.

20. The printer of claim 19 wherein:

a. the illumination from the gloss detector comprises a first wavelength at a first time and a second wavelength at a second time; and b. the controller provides the signal in response to: (1) a first ratio of the first reflection and the second reflection at the first time; and (2) a second ratio of the first reflection and the second reflection at the second time.

* * * * *